United States Patent [19]
Selby

[11] Patent Number: 5,692,832
[45] Date of Patent: Dec. 2, 1997

[54] VAPOR REMOVAL WITH APPARATUS GENERALLY TO NOT MACROSCOPICALLY DISTURB THE SURFACE OF A LIQUID SAMPLE THEREIN

[75] Inventor: Theodore W. Selby, Midland, Mich.

[73] Assignee: Tannas Co., Midland, Mich.

[21] Appl. No.: 517,429

[22] Filed: Aug. 21, 1995

Related U.S. Application Data

[63] Continuation-in-part of Ser. No. 425,588, Apr. 20, 1995.
[51] Int. Cl.$^6$ .................................................. G01N 25/56
[52] U.S. Cl. .................................... 374/54; 422/101
[58] Field of Search ............................ 374/54; 422/101, 422/103, 109

[56] References Cited

U.S. PATENT DOCUMENTS

| | | | |
|---|---|---|---|
| 2,116,442 | 5/1938 | McCluer | 422/101 X |
| 3,484,077 | 12/1969 | Porter | 422/103 X |
| 4,259,253 | 3/1981 | Najarian et al. | 422/109 |
| 4,689,237 | 8/1987 | Fabre | 426/521 |

OTHER PUBLICATIONS

Selby et al., "Engine Oil Volatility Studies—Generation of Phosphorus," 1995.
JPI-5S-41-93 (1993).
CEC-L-40-T-87 (1987).
Selby et al., "A New Approach to the Noack Volatility Test," Jan. 1994.
Selby et al., "Base Oil Characterization Techniques Using a New Approach to the Noack Volatility Test," 1994.
Schloemann, "Modified Noack Volatility Studies," Savant, Inc., Dec. 6, 1994.
Hydrick, *Lubricants World*, 4:12, Dec. 1994, pp. 7, 10–11 & 14.
Ace Glass, Inc., Catalog 1200, 1992, pp. 281–284, 353 & 382.
Roberts et al., "An Introduction to Modern Experimental Organic Chemistry," 2nd Edition, Holt, Rinehart and Winston, Inc., New York, 1974, pp. 36 & back page.
Rudy, "Cobalt (III) Complexes with (R)–1,2–Diaminopropane and Its Derivatives," W. Mich. U., M.A., 1985, University Microfilms, Ann Arbor, Mich., pp. 32–33.
Cole–Parmer Instrument Co., 1993–1994 Catalog, pp. 414–415.
Selby, "The Problems and the Opportunities in the Use and Reuse of Lubricating Oils to Meet the Needs of Modern Engines," 1994.

*Primary Examiner*—George M. Dombroske
*Assistant Examiner*—Paul D. Amrozowicz
*Attorney, Agent, or Firm*—Christopher John Rudy

[57] ABSTRACT

Vapors are removed from a vessel by a sweeping of a carrier gas gently above and/or across the surface of a solid or liquid sample and upward to an exit orifice. With an apparatus of the invention employed in a version of the sample volatility and vapor retrieval test, for example, the precision of high-yield vapor collection from lubricating oil samples at low pressure can be increased significantly and in some cases generally by an order of magnitude.

9 Claims, 2 Drawing Sheets

5,692,832

VAPOR REMOVAL WITH APPARATUS GENERALLY TO NOT MACROSCOPICALLY DISTURB THE SURFACE OF A LIQUID SAMPLE THEREIN

CROSS-REFERENCE

This is a continuation-in-part of U.S. patent application Ser No. 08/425,588 filed Apr. 20, 1995 pending. The same is incorporated herein by reference.

FIELD

In general, this invention concerns an apparatus and method useful for removal of vapor. In a particular embodiment, the invention concerns vapor removal from an oleaginous liquid, and in a more particular embodiment, it concerns vapor removal in a bench test.

BACKGROUND

Without question, in order to function, our society, with transportation and commerce therein, depends critically on the properties of certain liquids such as lubricating oils, transmission fluids, and so forth. Consequently, the determination of the properties of these liquids, so that each may be employed appropriately, is of great concern.

The Noack test is a standard procedure for determining the evaporation loss of an oil sample such as a lubricating or engine oil. See e.g., Japanese Standard JPI-55-41-93; European Standard CEC L-40-T-87.

Certain improvements to the Noack test have been developed and reported. See, Selby et al., "A New Approach to the Noack Volatility Test," presented 11–13 January 1994, Esslingen, Germany; Selby et al., "Base Oil Characterization Techniques Using a New Approach to the Noack Volatility Test," presented to the American Chemical Society in 1994; Schloemann, "Modified Noack Volatility Studies," presented to ASTM Committee D02.06.B/04.L, December 6, 1994, Atlanta, Ga.

A significant improvement in the art, applicable to the sample volatility and vapor retrieval test as well, is described by Selby et al., in parent U.S. patent application Ser. No. 08/425,588. Thereby, in general, a method to condense or coalesce matter is carried out by providing a suitable, narrow passageway for throughput of matter in a vapor state, and passing the matter in a vapor state through said passageway, under conditions such that the matter is coalesced into a more ordered state, and a matter coalescing apparatus has a hollow housing in communication with at least one of a plurality of suitably narrow hollow passageways, and a suitably narrow, elongately hollow, matter-coalescing passageway for throughput of matter to include as a vapor therein. Consequently, highly efficient yields of coalesced matter, to include liquid coalesced from vapor, even under only mild vacuum or at about ambient atmospheric pressure can be obtained thereby, especially so with respect to oils, where yields as high as 95 percent or greater can be obtained, without a general need for significant external cooling.

Nonetheless, in order to ascertain more reliably those properties of fluids, for example, oleaginous fluid samples in a sample volatility and vapor retrieval bench test, greater and greater precision is desired. Unfortunately, previous Noack and sample volatility and vapor retrieval bench test procedures could suffer from a lack of precision.

It would be desirable to provide ways and means to improve precision in the testing art, especially in a sample volatility and vapor retrieval bench test procedure. It would be further desirable if any solution to such problems had broader applicability.

SUMMARY

The present invention provides an apparatus useful for removal of vapor comprising the following components:

A) a hollow housing capable of holding a solid or liquid sample and being subject internally to a vacuum;

B) a hollow, carrier-gas wand in the housing having a carrier-gas entry port in communication with a carrier-gas system external to the housing, and a carrier-gas exit port disposed internally in the housing and at a position proximate the sample such that entering carrier-gas can sweep across a surface of the sample or through a section of vapor from the surface of the sample which is near thereto, but generally would not macroscopically significantly disturb the surface of the sample if a liquid; and C) an exit port in the housing for egress of carrier-gas/vapor from inside the housing.

Consequently, in general, vapors, as obtained by evaporation or sublimation, can be removed from such a vessel by a sweeping of the carrier gas gently above and/or across the surface of the sample and upward to the exit port. Also provided are methods of vapor retrieval and use of the apparatus.

The invention is useful in vapor retrieval broadly and in test procedures especially. In a particular embodiment, the invention is especially useful in vapor removal from an oleaginous liquid, and, in a more particular embodiment, vapor removal in the context of a sample volatility and vapor retrieval bench test.

Significantly, efficiency of vapor collection is greatly improved, as by the process of sweeping molecules above the surface away from the surface, and allowing new molecules to enter the vapor phase, or, in other words, as by "lifting the cloud" of the vapor up and out of the vessel with the carrier-gas provided inside the vessel housing by the special wand placement. With such improved efficiency, reproducibility of data collection can become highly advanced. For example, precision of high yield vapor collection at low pressure is increased dramatically with an apparatus of the invention when employed in a significantly improved progeny of both the Noack test and the Selby et al. sample volatility and vapor retrieval test, which employs a fluid coalescing method and apparatus of the parent application in addition to other improvements, notably among which is the collection or retrieval of volatilized sample by coalescing. In some cases, the precision can be improved generally by an order of magnitude over results obtained from previous test procedures.

Numerous further advantages attend the invention.

DRAWINGS

The drawings form part of the specification hereof. In the drawings, the following is noted:

ILLUSTRATIVE DETAIL

The invention can be further understood from the present detail, taken in view of the accompanying drawings and the incorporated matter. The same generally is to be construed as illustrative and not necessarily limiting in nature.

Figures 1, 2:
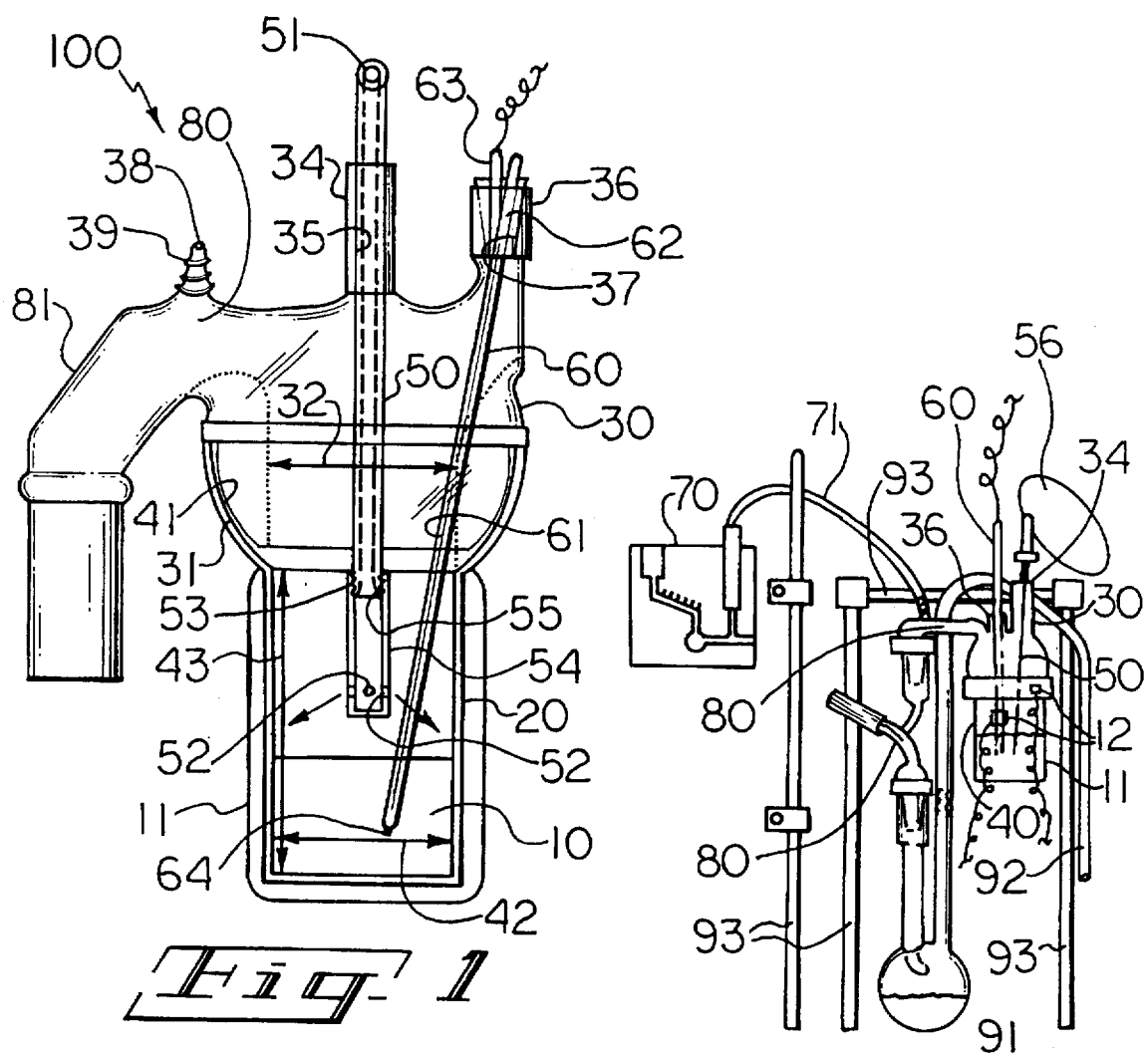
FIG. 1 is a side plan view of an apparatus of the present invention.
FIG. 2 is a side view of an apparatus of the invention more fully set up for operation.

In reference to the drawings, especially FIGS. 1 & 2, apparatus 100 for vaporizing sample 10 has hollow housing 20 which is capable of being subject to an internal vacuum and of holding the sample 10, for example, an engine oil, transmission fluid, or other oleaginous liquid, and so forth, as for vapor volatility testing. The housing 20 may be composed of separable top cover 30 and bottom flask 40, for example, as generally of glass connectable with mating ground glass joints 31 & 41, say, of a domed or convexo-concavo configuration, respectively, say, in a size 75/50. Such a mating arrangement has significant advantages in test procedures of preventing "freezing" of the joints and of generally eliminating the trapping of volatilized, condensed liquid thereat. Also, a lubricant may not be required. The housing may be one-piece, but a separable housing is preferred for ready manufacture, set-up, take-down, clean-up, storage, repair and/or replacement. Preferably, the shape of the top cover 30 internally is generally cylindrical, for example, with an inside diameter 32 of 5.2 centimeters (cm) or so and a general inside height 33 of 6.0 cm or so, ports of ingress and egress taken into additional account, and externally may be generally semi-spheroid or semi-ellipsoid, ports of ingress and ingress taken into additional account as well. Advantageously, particularly when intended for sample volatility and vapor retrieval bench test procedures, the shape of the bottom flask 40 is generally cylindrical, especially of an inside diameter generally the same as that of the top cover 30, for example, with the bottom flask 40 having an inside diameter 42 of 5.2 cm or so and a cylinder inside height 43 of 7.0 cm or so. Otherwise, the housing 20, top cover 30, and bottom flask 40 may be of any suitable shape. Desirably, the housing 20 is heated, especially by an externally positioned, noble metal electric heater 11 with couplings 12 to receive power from a suitable electric power supply, so as to heat and cause vaporization of the sample 10.

The housing 20, for example, in the top cover 30, may have sealable carrier-gas wand port 34 for insertion of a carrier-gas wand 50 such as provided by a standard female ground glass joint 35, say, of size 10/30 or 24/40, and so forth. Another sealable port 36 may be present in the housing 20 or, say, top 30 thereof, which may be employed for insertion of a temperature-measuring sensor 60 such as provided by a standard female ground glass joint 37. A further port 38 may be provided the housing 20 or top 30 thereof which may be employed as a port for attachment of a vacuum monitoring device 70 such as a manometer, for example, a DURABLOCK (Reg. U.S. Pat. & Tm. Off.) manometer as described in U.S. Pat. No. 1,917,637 and available from Dwyer Instruments Co., Michigan City, Ind., actuatable through connection of tubing 71, say, of ⅛-inch (0.32-cm) outside diameter TYGON (Reg. U.S. Pat. & Tm. Off.) plastic, slipped over tube-holding ridges 39. Other means to connect components at ports such as by threads and so forth may be employed.

Figure 3A:
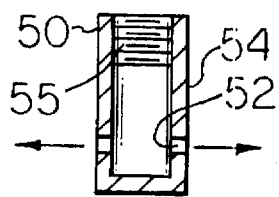
FIGS. 3A, 3B, 3C, 3D, 3E, 3F, 3G, 3H & 3I are views of further carrier gas wand embodiments of the invention.
Figure 3B:
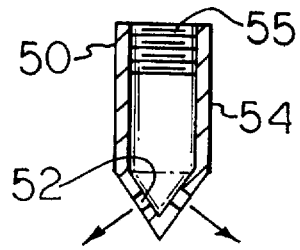
Figure 3C:
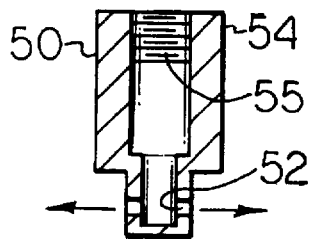
Figure 3D:
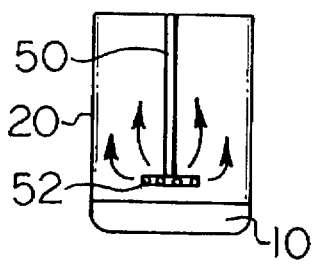
Figure 3E:
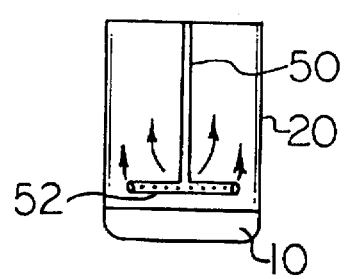
Figure 3F:
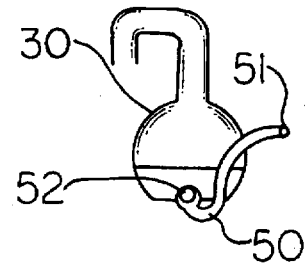
Figure 3G:
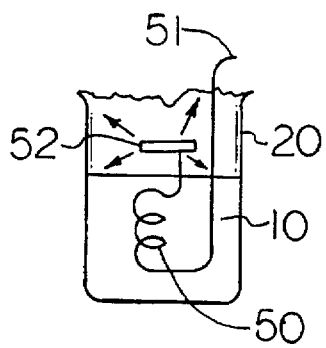
Figure 3H:
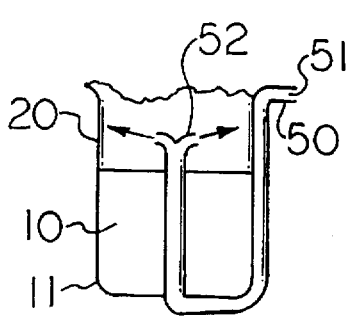
Figure 3I:
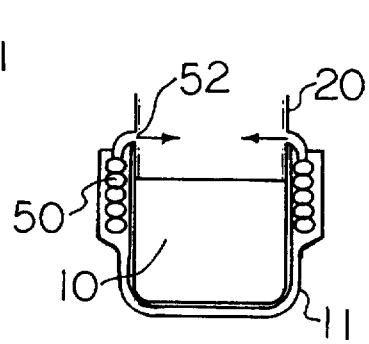

As shown in FIGS. 1–3, the apparatus 100 has at least one hollow, carrier-gas wand 50 made of a suitable material such as glass or metal, for example, of heat-resistant glass, copper or stainless steel, present with the housing 20, and it may be extend from a top cover 30 as shown in FIGS. 1, 2, 3F & 3G. As an alternative, the wand 50 may extend from a bottom flask 40 part of a housing 20 having multiple housing parts as shown in FIG. 3H, or it may be provided by ports emanating from the housing itself as shown in FIG. 3I. The hollow wand 50 may be heated so as to heat the carrier-gas which would flow through it such as may be carried out by running it under the test sample 10, especially if the sample 10 is a liquid as shown in FIG. 3G; imbedding the wand about the heater, e.g., heater 11 as shown in FIGS. 3H & 3I; and/or or analogously positioning or embedding it where drawn-off hot vapors can heat it and concurrently cool themselves for more efficient collection. Significantly, especially in the context of sample testing, pre-heating the carrier gas in the wand, for example, to a temperature at or about that of the pre-vaporized, heated sample, can have the desirable trait of removing a variable, thus making such a test more internally consistent and reliable. Carrier-gas wand 50 may be separable from the housing 20, as, say, through standard male joint 51 for mating with the standard female joint 32. As an alternative, the wand 50 may be permanently affixed to or integral with the housing 20, say, by being made of the same material as the housing 20 is made of, for example, of blown glass, as depicted in FIG. 3F. The carrier-gas wand 50 has a carrier-gas entry port 51 for communication with, and hence supply by, a carrier-gas system external to the housing. The carrier-gas system and supply may be provided by ambient or bottled air, or other suitable bottled or generated gas supply such as of one or more of nitrogen, oxygen, carbon dioxide, helium, argon, methane, ethane, propane and so forth and the like. Ambient air is typically employed as the carrier-gas system and supply. The hollow wand 50 also has a carrier-gas exit port 52. The wand carrier-gas exit port(s) 52 is(are) disposed or positioned internally in the housing 20 at a position proximate the sample 10, which is typically under the influence of gravity so that port(s) 52 is(are) at a position above the surface of the solid or liquid sample 10, such that entering carrier-gas can sweep across a surface of the sample 10, say again, its top surface, or through a section of vapor from the surface of the sample 10 which is near thereto, again when under the influence of gravity as its top surface. For example, in the context of the volatility and vapor recovery testing procedure, a wand exit port 52 can be advantageously disposed at a position from ½ an inch (1.28 cm) to 1-½ inches (3.82 cm) above the initial surface of the test sample 10 of oil, with desirable results being obtained at an 0.8-inch (2.03-cm) or so interval above the initial test oil sample 10. So as to improve the ability of the operator to adjust such an interval of the carrier-gas wand exit port(s) away from the surface of the sample 10, the wand 50 may be provided with threads 53, onto which wand cap 54 having threads 55 can be screwed. In general, during operation, the sweeping would not macroscopically significantly disturb the surface of the sample 10 if the sample 10 is a liquid as in the more typically encountered case. Optional vapor trap balloon 56 can be employed in test procedures to trap volatilized vapors during warm-up of the apparatus 100, returning the trapped vapors to the inside of the housing at the beginning of a test run by gently squeezing the balloon to release its vapor contents proximate carrier-gas entry port 51. Preferably, as in progeny sample volatility and vapor retrieval bench testing procedures, the balloon 56 is removed from the wand 50 and is squeezed to release its trapped vapor immediately adjacent the carrier-gas entry port 51.

Preferably, especially in the context of controlled-temperature experimental apparatus, the apparatus 100 has temperature-measuring sensor 60. This can be provided by a small diameter, thin-walled, stainless steel tube 61 including in addition a standard size, male, ground stainless steel joint 62. Through the hollow stainless steel tube 61 can be inserted electrical thermocouple 63 with exposed sensing end 64, which may be inserted an appropriate distance into the sample 10. Sensor 60 components can be made and sealed in such a manner that the sensing end 64 protruding through the bottom of the tube 61 is exposed directly to the sample 10. Preferably, the tube 61 and sensing end 64 are sealed so that the necessary vacuum can be maintained during liquid sample volatility and vapor retrieval bench testing.

As shown in FIGS. I & 2, the apparatus 100 has at least one exit port 80 in the housing 20 for egress of carrier-gas/vapor from inside the housing 20. The exit port 80 advantageously can be in the form of exit arm 81 directed toward a source of gravity so as to avoid undesirable potential for reflux of volatilized vapors. The exit arm 81 may terminate in a connector 82, which may take the form of a ground joint, for example, a standard 24/40-sized ground glass male joint which can be connected with standard corresponding female connection to a 0–3-millimeter (mm) adjustable needle valve containing coalescer 90 as described by Selby et al., in the aforementioned, incorporated parent hereto. The coalescer 90 has recovered sample container 91 to which is connected vacuum line 92 which is connected to a vacuum source such as a vacuum pump. Frame 93 may support the apparatus 100.

The following examples further illustrate the invention. Therein, parts and percentages are by weight unless otherwise specified or ascertainable by the context.

EXAMPLE 1

The apparatus of FIG. 2 is cleaned. To the tared bottom flask of the apparatus with a single, downwardly-directed, 0.082-inch carrier-gas exit port is added a measured weight of standard reference Noack oil sample (14.2 percent volatiles). The entire apparatus is assembled so that the carrier-gas exit port is 0.818 inches above the surface of the oil sample. Connections are checked for snugness. The manometer is checked and re-zeroed. The balloon vapor trap is squeezed to remove excess air and is connected to the carrier-gas entry port of the carrier-gas wand, drawing between 0.5 and 1.0 inches of water vacuum which quickly equilibrates back to ambient atmospheric pressure. The noble metal heating element and thermocouple are activated. When the temperature reads about 246 degrees C., the balloon vapor trap is pinched to prevent loss of its trapped vapor and is removed. Upon equilibration of the manometer to zero and the temperature reaching 249 degrees C., a timer is started for a 1-hour interval. Immediately, with a vacuum pump activated, the vacuum is controlled to 0.8 inches of water with the needle valve on the coalescer. Once flow has started, the balloon vapor trap is released directly above the carrier-gas entry port to promote vapors entering the vessel.

Upon completion of the 1-hour interval, the heat and vacuum are turned off. After waiting for a 10-minute interval, the recovered sample container is removed and weighed, and compared to its tare weight. After waiting for an additional 20-minute interval (half an hour after the heat and vacuum are turned off) the bottom flask is removed and weighed, and compared to its sample-containing weight.

The procedure is repeated four times, and the error determined to be about 2 percent. This is well within the typical error encountered in the known Noack test procedure of some 5 to 10 percent.

EXAMPLE 2

Following the procedure of Example 1, five series of runs are carried out with various other reference oils, and the following percent loss results are reported:

|  | ASTM #1 | ASTM #2 | ASTM #3 | ASTM #4 | ASTM #5 |
|---|---|---|---|---|---|
| Run 1: | 18.66 | 13.00 | 19.95 | 22.86 | 16.27 |
| Run 2: | 18.63 | 12.90 | 19.15 | 23.12 | 15.85 |
| Run 3: | 18.54 | 13.00 | 22.31 | 22.41 | 15.15 |
| Run 4: | 18.68 | 13.17 | 20.42 | 22.93 | 16.42 |
| Mean 1–4: | 18.63 | 13.02 | 20.46 | 22.83 | 15.93 |
| Median 1–4: | 18.64 | 13.00 | 20.19 | 22.90 | 16.06 |
| Std. Deviation 1–4: | 0.06 | 0.11 | 1.34 | 0.30 | 0.56 |
| Standard Error 1–4: | 0.03 | 0.06 | 0.67 | 0.15 | 0.28 |
| Total Percent Error: | 0.3 | 0.8 | 6.6 | 1.3 | 2.5 |

CONCLUSION

The present invention is thus provided. Numerous modifications can be effected within its spirit, the literal claim scope of which is particularly pointed out as follows.

I claim:

1. An apparatus useful for removal of vapor comprising the following components:
    A) a hollow housing having at least two basic, connectable portions: a top cover, and bottom flask; which housing is capable of holding a solid and liquid sample in its bottom portion, which bottom flask portion has an interior that is generally cylindrical, and which housing is capable of being subject internally to a vacuum when the top cover and bottom flask portions are connected suitably;
    B) a hollow, carrier-gas wand in the housing having a carrier-gas entry port in communication with a carrier-gas system external to the housing, and a carrier-gas exit port disposed internally in the housing and centrally with respect to generally cylindrical boundaries of the housing which are laterally disposed thereabout and at a position proximate and above a position where the sample can be held such that entering carrier-gas can sweep across a surface of the sample or through a section of vapor from the surface of the sample which is near thereto, but generally not macroscopically significantly disturb the surface of the sample;
    C) an exit port in the housing for egress of carrier-gas/vapor from inside the housing; and
    D) at least one port additional to the exit port.

2. The apparatus of claim 1, wherein a thermocouple is present.

3. The apparatus of claim 2, wherein the top cover and bottom flask are made with glass and are connectable with convexo-concavo ground glass joints.

4. The apparatus of claim 3, wherein the housing is generally cylindrical, save the exit port and additional port (s) to include for at least one of the carrier-gas wand and the thermocouple and the bottom flask has an externally positioned, noble metal electric heater which can heat the sample; further wherein a vapor trap balloon for attachment to a port of the housing is present.

5. A method of vapor removal for an oleaginous liquid comprising the following steps:
    A) providing an apparatus comprising the following components:
        1) a hollow housing capable of holding an oleaginous liquid and being subject internally to a vacuum;
        2) a hollow carrier-gas wand in the housing having a carrier-gas entry port in communication with a carrier-gas system external to the housing, and a carrier-gas exit port disposed internally in the housing and centrally with respect to generally cylindrical boundaries of the housing which are laterally disposed thereabout and at a position proximate and above said liquid such that entering carrier-gas can sweep across a surface of said liquid or through a section of vapor from the surface of said liquid which is near thereto, but generally not macroscopically significantly disturb the surface of said liquid; and 3) an exit port in the housing for egress of carrier-gas/vapor from inside the housing;

B) providing the oleaginous liquid and a carrier-gas to the apparatus housing and heating said liquid to volatilize the same; and C) sweeping molecules above the surface away from the surface, and allowing new molecules to enter the vapor phase, as by lifting the vapor up and out of the housing with the carrier-gas provided inside the vessel housing by the wand placement without macroscopically significantly disturbing the surface of the oleaginous liquid.

6. The method of claim 5, wherein a vacuum is employed, and the vapor is coalesced by employment of a needle-valve through which the vapor travels after passing through the exit port.

7. A method of testing an oleaginous liquid sample comprising the following steps:

A) providing an apparatus comprising the following components:

1) a hollow, at least in substantial part generally cylindrical housing-saving in an exit port and any additional port(s) of the housing, which housing has a heater for heating of the oleaginous liquid sample to be contained therein, the housing capable of holding said sample in a generally cylindrical bottom portion thereof and being subject internally to a vacuum;

2) a hollow, carrier-gas wand in the housing having a carrier-gas entry port in communication with a carrier-gas system external to the housing, and a carrier-gas exit port disposed internally in the housing and centrally with respect to lateral, generally cylindrical boundaries of the housing which are laterally disposed thereabout and at a position proximate and above said sample such that entering carrier-gas can sweep across a surface of said sample or through a section of vapor from the surface of said sample which is near thereto, but generally not macroscopically significantly disturb the surface of said sample; and 3) the exit port in the housing for egress of carrier-gas/vapor from inside the housing;

B) providing the oleaginous liquid sample and carrier-gas to the apparatus housing and, under vacuum, heating said sample with the housing heater to volatilize said sample;

C) sweeping molecules above the surface away from the surface, and allowing new molecules to enter the vapor phase, as by lifting the vapor up and out of the housing with the carrier-gas provided inside the vessel housing by the wand placement without macroscopically significantly disturbing the surface of the oleaginous liquid sample;

D) coalescing the volatilized vapor through a coalescer containing a constriction in a throughput channel; and E) measuring a weight difference of volatilized sample.

8. The method of claim 7, wherein the housing is basically of two-piece, glass construction; the heater is an externally positioned, noble metal electric heater; and the carrier-gas is air.

9. The method of claim 8, wherein percent error of a series of runs in about 2.5 percent or less.

* * * * *